United States Patent
Longo, Jr. et al.

(10) Patent No.: US 8,574,555 B2
(45) Date of Patent: Nov. 5, 2013

(54) STABLE ONE-PART AQUEOUS TOOTH WHITENING COMPOSITION

(75) Inventors: James J. Longo, Jr., Wilmington, DE (US); William A. McHale, Collegeville, PA (US)

(73) Assignee: Premier Dental Products Company, Plymouth Meeting, PA (US)

( * ) Notice: Subject to any disclaimer, the term of this patent is extended or adjusted under 35 U.S.C. 154(b) by 0 days.

(21) Appl. No.: 11/670,229

(22) Filed: Feb. 1, 2007

(65) Prior Publication Data

US 2007/0202059 A1 Aug. 30, 2007

Related U.S. Application Data

(60) Provisional application No. 60/764,072, filed on Feb. 1, 2006.

(51) Int. Cl.
*A61K 8/22* (2006.01)
*A61K 8/81* (2006.01)

(52) U.S. Cl.
USPC .............................. 424/53; 424/49; 424/78.25

(58) Field of Classification Search
USPC .......................................................... 424/53
See application file for complete search history.

(56) References Cited

U.S. PATENT DOCUMENTS

| | | | |
|---|---|---|---|
| 5,032,178 A | 7/1991 | Cornell | |
| 5,059,417 A | 10/1991 | Williams et al. | |
| 5,171,564 A | 12/1992 | Nathoo et al. | |
| 5,759,440 A | 6/1998 | Van Hemelrijk | |
| 5,908,614 A | 6/1999 | Montgomery | |
| 5,922,307 A | 7/1999 | Montgomery | |
| 5,944,528 A | 8/1999 | Montgomery | |
| 6,162,055 A | 12/2000 | Montgomery et al. | |
| 6,221,341 B1 | 4/2001 | Montgomery | |
| 6,312,670 B1 | 11/2001 | Montgomery | |
| 6,322,773 B1 | 11/2001 | Montgomery | |
| 6,331,292 B1 | 12/2001 | Montgomery | |
| 6,343,933 B1 | 2/2002 | Montgomery et al. | |
| 6,348,518 B1 | 2/2002 | Montgomery | |
| 6,458,340 B1 | 10/2002 | Ibsen et al. | |
| 6,472,453 B2 | 10/2002 | Montgomery | |
| 6,475,469 B1 | 11/2002 | Montgomery | |
| 6,479,037 B1 | 11/2002 | Montgomery | |
| 6,485,709 B2 | 11/2002 | Banerjee et al. | |
| 6,488,914 B2 | 12/2002 | Montgomery | |
| 6,500,408 B2 | 12/2002 | Chen | |
| 6,514,543 B2 | 2/2003 | Montgomery | |
| 6,536,628 B2 | 3/2003 | Montgomery | |
| 6,824,704 B2 | 11/2004 | Chadwick et al. | |
| 6,908,607 B2 | 6/2005 | Banerjee et al. | |
| 6,958,144 B2 | 10/2005 | Montgomery | |
| 2004/0219111 A1 | 11/2004 | Kim et al. | |
| 2005/0008584 A1 * | 1/2005 | Montgomery | 424/53 |
| 2005/0123502 A1 | 6/2005 | Chan et al. | |
| 2006/0051384 A1 * | 3/2006 | Scholz et al. | 424/405 |
| 2006/0147394 A1 | 7/2006 | Shastry et al. | |
| 2008/0145321 A1 | 6/2008 | Zaidel et al. | |

FOREIGN PATENT DOCUMENTS

| | | |
|---|---|---|
| WO | WO 97/11676 | 4/1997 |
| WO | WO 98/30494 | 7/1998 |
| WO | WO 2005/070378 | * 8/2005 |
| WO | WO 2005/097053 | 10/2005 |

OTHER PUBLICATIONS

Davidson et al., In-Mouth Measurement of pH and Conductivity during Eating, J. Agric. Food Chem., 1998, 46, pp. 5210-5214.*
ISP, A Product Guide, 2005, http://online1.ispcorp.com, pp. 1-20.*
International Searching Authority, International Search Report and Written Opinion, Sep. 25, 2007.

* cited by examiner

*Primary Examiner* — Walter Webb
(74) *Attorney, Agent, or Firm* — Cozen O'Connor

(57) ABSTRACT

The invention relates to a high-temperature stable, one-part, aqueous tooth bleaching composition for contacting a tooth surface. The composition comprises a bleaching agent comprising a high level of a aqueous hydrogen peroxide. The bleaching agent is derived from multiple components within the composition and comprises at least about 15% by weight of the total composition weight. The Composition also comprises a bleaching agent stabilizer comprising from about 0.01% to about 1.00% by weight of the total composition weight.

17 Claims, No Drawings

STABLE ONE-PART AQUEOUS TOOTH WHITENING COMPOSITION

CROSS-REFERENCE TO RELATED APPLICATIONS

The present application claims the benefit of U.S. Provisional Application No. 60/764,072 filed on Feb. 1, 2006, which is incorporated herein by reference

STATEMENT REGARDING FEDERALLY SPONSORED RESEARCH OR DEVELOPMENT

The present invention was not developed with the use of any Federal Funds, but was developed independently by the inventor.

BACKGROUND OF THE INVENTION

Tooth bleaching typically involves the application of a peroxide containing composition to the surface of the tooth enamel to achieve a desired whitening effect. The most common peroxide donor ingredients are, but are not limited to, carbamide (urea) peroxide and hydrogen peroxide. The latter has become the tooth bleaching material of choice due to its ability to whiten teeth faster than higher concentrations of carbamide peroxide. Additionally, aqueous tooth whitening gels have proven desirable due to the hydrating effects on the structure of the tooth, reducing the likelihood of tooth sensitivity. As such, it is desirable to achieve stable aqueous hydrogen peroxide tooth whitening gels for commercial preparation.

Aqueous hydrogen peroxide tooth bleaching formulations have their limitations however. Until recent years, stable aqueous hydrogen peroxide tooth bleaching gels have been virtually non-existent. Hydrogen peroxide is a powerful oxidizing agent and an unstable compound that decomposes readily over time into water and oxygen. Certain chemical and physical influences can accelerate the rate of decomposition and need to be controlled for a stable tooth whitening gel to exist. Temperature, pH and errant metal ions all have a profound effect on the decomposition of hydrogen peroxide, particularly in an aqueous formula. Aqueous tooth whitening gels comprising high levels of hydrogen peroxide are defined as comprising an available hydrogen peroxide concentration equal to or greater than about 15% of the total composition weight up to and including about 40% of the total composition weight. Generally, these high level hydrogen peroxide compositions require the gel to be refrigerated to reduce the rate of decomposition, thus enabling an increased shelf life. This process is difficult as well as expensive for commercial distributors to maintain adequate shelf life for salable product.

To combat these limitations, high level hydrogen peroxide bleaching compositions are generally delivered to the end user in a two-part system packaged form that maximizes peroxide stability. Packaging stabilized hydrogen peroxide solutions separately from other formulation ingredients is one method that enables manufacturers to meet required shelf life parameters. Two types of separation methods are dual barrel syringes and liquid hydrogen peroxide/powder systems. The disadvantages to these types of packaging are that the hydrogen peroxide must be mixed at the time of placement in the dental operatory, thus resulting in a loss of valuable chair time and the unwillingness for patients to prolong the tooth whitening experience. Additionally, due to hydrogen peroxide's highly corrosive properties, peroxide burns from the splatter resulting from the spatulation of the mix process are always a concern. There also exists the potential for a non-homogeneous mix In office bleaching by dentists is the primary end use for high level hydrogen peroxide tooth whitening compositions. Therefore, it is imperative that the whitening compositions be formulated as one-part (no-mix) systems and maintain adequate shelf stability in order to guarantee efficacy at the time of placement by the dentist within the patient.

Most distributors of in-office dental products require that a suitable shelf life be maintained for any given product. Further, most distributors rely on a product to maintain a two year shelf stability. Shelf stability is generally determined amount of time to ensure a abnormal or exaggerated storage conditions for a predetermined amount of time to ensure a product's stability under normal storage conditions. Room temperature storage conditions, for a single component tooth bleaching composition, are desirable in order to eliminate costly and inconvenient storage problems. To a greater degree, a two year room temperature storage guarantee is what is required for distribution of a single component aqueous tooth bleaching composition.

The pH of an aqueous hydrogen peroxide tooth whitening composition also has great bearing on the stability of the gel. Hydrogen peroxide solutions are strongly acidic and maintain their stability in acidic pH formulas. Stable aqueous hydrogen peroxide tooth whitening gels can be formulated in the acid pH range. However, bleaching compositions in the acidic pH range (pH 2.0-5.5) are prone to the demineralization of dental enamel by the solublizing of calcium ions from the tooth surface. This reduction in surface enamel leads to tooth sensitivity and discomfort for the patient.

Additionally, it has been shown that peroxide containing tooth bleaching compositions are more effective at whitening teeth at higher pH levels than at lower pH level. Therefore it is desirous to obtain a single component, aqueous tooth bleaching composition with high levels of hydrogen peroxide that can maintain a non-refrigerated, two year shelf stability while exhibiting a neutral or basic pH or a pH of greater than about 5.5. Unfortunately, to date, no such commercial formula exists.

Recent technology has shown single component, high-level aqueous hydrogen peroxide gels to be stable for short periods of time at room temperature. It is known that the presence of stabilizing agents within the aqueous hydrogen peroxide tooth whitening formula can extend the life of the formula by slowing or eliminating the rate of peroxide decomposition. Decomposition of the peroxide within the formula can result in viscosity loss of the composition, expansion of the composition due to the evolution of oxygen gas and/or the loss of available hydrogen peroxide content.

U.S. Pat. No. 6,555,020 to Chadwick et al disclose stable aqueous tooth whitening compositions containing high levels of hydrogen peroxide. Chadwick teaches the utilization of aminocarboxylic acid/salt stabilizing agents to prolong room temperature shelf stability and to maintain the gel characteristics of the composition. The stabilizing agents are selected from a group consisting of CaNa2EDTA, Na4EDTA, and CDTA. However, Chadwick discloses that the greatest shelf stability is for a term of 84 under room temperature storage conditions. While 84 days (12 weeks) is a significant stability period for an elevated hydrogen peroxide level tooth whitening formula, it fails to show long-term stability under exaggerated conditions and can only be translated into a 12 week stability period for the composition. Thus, it falls considerably short of a desired two year shelf life required to become a salable product through commercial distribution.

U.S. Pat. No. 5,858,332 to Jensen et al. teach of a stable, one-part, premixed hydrogen peroxide tooth whitening composition that utilizes a bleaching agent stabilizer that ties up errant metal ions that can result in decomposition of the bleaching agent within the tooth whitening composition. Jensen et al. describes a bleaching agent selected from a group consisting of aqueous hydrogen peroxide, carbamide peroxide, sodium perborate and mixtures thereof. Additionally, the whitening composition comprises a single thickenening agent, a carrier, and a bleaching agent stabilizer selected from a group of edetate disodium, EDTA, oxine EDTA, calcium disodium EDTA, adipic acid, succinic acid, citric acid, tin nitrates, tin phosphates and mixtures of the foregoing.

Jensen et al. claim a stable one-part dental bleaching agent that maintains at least 95% of its original strength 1 month after its manufacture and at least 60% approximately 3 months after the compositions manufacture. However, Jensen et al. makes no mention of the stability under exaggerated and/or accelerated storage conditions and it is understood that the stability occurs under room temperature conditions and for a maximum of 60-95% available hydrogen peroxide content after 3 months storage time.

U.S. Pat. Nos. 6,488,914; 6,331,292 and 6,221,341 to Montgomery detail aqueous tooth whitening compositions with neutral or alkaline pH levels. Montgomery teaches one-part, aqueous tooth whitening compositions that are formulated to be stable at high pH levels (6-10). The significance of this teaching is the ability to detail an aqueous hydrogen peroxide tooth whitening composition that is stable under neutral or alkaline conditions with a high water content within the composition (>70%). However, Montgomery claims an available hydrogen peroxide content of less than 15% of the total weight of the composition, which falls far short of an elevated or high hydrogen peroxide concentration within the composition. Additionally, Montgomery makes no mention of extended storage stability as well as the stability of the compositions under exaggerated or accelerated temperature conditions.

U.S. Pat. No. 6,500,408 to Chen details a tooth bleach that utilizes Polyvinylpyrrolidone as a thickening agent in combination with hydrogen peroxide. However, Chen stipulates that the PVP must be present in the formula at a concentration of 25% or greater. He makes no mention of multiple thickening agents within the composition, nor is the PVP thickening agent a cross linked, polyplasdone polymer/hydrogen peroxide complex, contributing synergistically to the available hydrogen peroxide within the total bleach composition. Additionally, Chen makes no mention of long term elevated temperature stability of the tooth bleaching composition.

In contrast, the present invention relates to stable one-part, aqueous tooth whitening composition that utilizes high levels of hydrogen peroxide bleaching agent in a neutral gel formula (pH 6-7). The stability of the composition is proven under accelerated and/or exaggerated storage conditions which translate into at least a two year shelf life for the composition under normal room temperature storage conditions. The stability of the composition is a critical function of known tooth whitening ingredients combined under unique parameters including weight percentages and ratios, for the elevated temperature stability to occur. Deviation outside the controlled composition window, results in predictable failure of the composition.

BRIEF SUMMARY OF THE INVENTION

The invention relates to a high-temperature stable, one-part, aqueous tooth bleaching composition for contacting a tooth surface. The composition comprises a bleaching agent comprising a high level of a aqueous hydrogen peroxide. The bleaching agent is derived from multiple components within the composition and comprises at least about 15% by weight of the total composition weight. The Composition also comprises a bleaching agent stabilizer comprising from about 0.01% to about 1.00% by weight of the total composition weight.

In one preferred embodiment, the bleaching agent is derived from multiple components within the composition including an aqueous hydrogen peroxide, a polyplasdone hydrogen peroxide complex; a polyacrylic acid polymer; water; glycerin; ethylenediaminetetraacetic acid, disodium salt; etidronic acid and ammonium hydroxide.

In one preferred form of the invention, the bleaching agent stabilizer comprises a 1:1 ratio of ethylenediaminetetraacetic acid, disodium salt and etidronic acid. The ratio of hydrogen peroxide to bleaching agent stabilizer is about 25:1 to about 60:1. And, the ratio of hydrogen peroxide to bleaching agent stabilizer is about 25:1 to about 60:1. The bleaching agent stabilizer may be selected from a group consisting of ethylenediamineteraacetic acid, disodium salt; ethylenediamineteraacetic acid, tetrasodium salt; ethylenediaminetetraacetic acid, calcium disodium salt; etidronic acid; citric acid; gluconic acid; sodium citrate; sodium gluconate; sodium phosphate; disodium phosphate; trisodium phosphate; tetrapotassium pyrophosphate; sodium tripolyphosphate and potassium stannate.

The tooth bleaching composition may also include a plurality of thickening agents, the thickening agents comprising at least a crosslinked polyacrylic acid polymer and a polyplasdone hydrogen peroxide complex. In one form of the invention, The crosslinked polyacrylic acid thickening agent comprises less than about 1.50% by weight of the total composition weight. The thickening agents may comprise from about 5.0% to about 50.0% by weight of the total composition weight. And, the polyplasdone hydrogen peroxide complex may comprise at least about 10.0% by weight of the total composition weight.

The tooth bleaching composition may also include at least one chelating agent selected from the group consisting of ethylenediamineteraacetic acid, disodium salt; ethylenediamineteraacetic acid, tertrasodium salt, ethylenediaminetetraacetic acid, calcium disodium salt; citric acid; gluconic acid; sodium citrate; sodium gluconate; sodium phosphate; tripolyphosphate. The at least one chelating agent may comprise from about 0.01% to about 0.50% by weight of the total composition weight. In one preferred embodiment, the chelating agent, the chelating agent(s) may be disodium EDTA and/or etidronic acid.

The tooth bleaching composition may also include at least one hygroscopic agent selected from the polyol group consisting of glycerin, polyethylene glycol and sorbitol. The at least one hydroscopic agent may comprise from bout 1.0% to about 10.0% by weight of the total composition weight. In one preferred embodiment, the hygroscopic agent is glycerin.

The tooth bleaching composition may also include at least one neutralizing agent selected from a group consisting of triethanolamine, tromethamine, sodium hydroxide, potassium hydroxide, and ammonium hydroxide. The at least one neutralizing agent may adjust the pH of the final tooth whitening composition between about 6.0 to about 7.0. The at least one neutralizing agent may comprise from about 0.50% by weight of the total composition weight. In one preferred embodiment, the at least one neutralizing agent is ammonium hydroxide.

DETAILED DESCRIPTION OF THE INVENTION

The present invention is direct to a stable, one-part, aqueous tooth whitening compositions containing high percentages of bleaching agent stable at elevated storage temperatures for extended periods of time. In particular, the invention relates to compositions that comprise a hydrogen peroxide bleaching agent derived from multiple sources present within the aqueous tooth bleaching formula acting synergistically to release elevated levels of peroxide to the tooth surface for a desired whitening effect while remaining stable with no appreciable decomposition of the bleach composition when subjected to accelerated stability testing involving storage temperatures from 40 degrees C. to 47 degrees C. for a predetermined amount of time.

The tooth whitening compositions exhibit high temperature stability, based on retention of available hydrogen peroxide and net viscosity loss. Stability is defined as the ability of the composition not to lose more than about 10% of the gels initial available hydrogen peroxide content through about a 2 year time frame and remaining viscous and substantially free of entrained oxygen bubbles resulting from decomposition of the peroxide. The bleach compositions representative of the present invention were tested through two elevated temperature storage conditions: about 40 degress C. and about 47 degrees C. depending upon available hydrogen peroxide content within the composition. The compositions maintain greater than 95% available hydrogen peroxide content after 12 weeks storage at 40 degrees C. (104 degrees F.) with no loss of gel viscosity. After 15 weeks at 40 degrees C., the compositions exhibit retention of greater than 94% available hydrogen peroxide with little to no viscosity loss and greater than 90% available peroxide retention after 20 weeks with a slight loss in viscosity and pH. It should be understood that under accelerated stability testing protocol, a product formulation must survive for a minimum of 12 weeks at 40 degrees C. in order to be assumed that it will survive on the open market for a minimum of two years under room temperature storage conditions (i.e. non-refrigerated storage). Likewise, a product formulation must survive for a minimum of 9 weeks at 47 degrees C. to assume the same two year room temperature stability.

In one preferred composition, a hydrogen peroxide content of about 15 to 32% survived for an excess of 12 weeks at 40 degrees C. with little to no loss of available hydrogen peroxide content. In a further preferred composition, a gel with a hydrogen peroxide content of about 15 to 32% survived in excess of 4 weeks and 6 days at 47 degrees C. with less than a 10% available hydrogen peroxide loss within the composition. In the most preferred composition, a hydrogen peroxide content of 15% to 20% survived in excess of 9 weeks at 47 degrees C. with little to no loss of available hydrogen peroxide content.

Critical to the stability of the compositions are the presence of one or more chelating or stabilizing agents incorporated in a precise ratio to the level of peroxide content within the formula creating a narrow window for elevated temperature stability to occur. Deviation outside the accepted window results in predictable failure for the whitening composition under the elevated temperature storage conditions. In addition, the pH of the final composition has a narrow hand in which stability of the gel will occur as well. A pH that is greater than the upper limit threshold of the composition will result in predictable failure for the whitening composition. Stabilized aqueous hydrogen peroxide is the preferred bleaching agent with a minimum peroxide starting content of 35 to 50%.

It is the purpose of this application to describe the preferred embodiments of a tooth bleaching composition made in accordance with the present invention. The preferred tooth bleaching composition contains high levels of hydrogen peroxide and exhibits stability at elevated storage temperatures. The present invention relies on a specific mixture of ingredients combined under tight tolerances and specific mix procedures to attain a stable, one-part bleaching gel that can survive a two year, non-refrigerated shelf life as required for commercial distribution.

Hydrogen peroxide in its aqueous form is the preferred primary peroxide source. Stabilized hydrogen peroxide solutions are available commercially from a number of chemical manufacturers. The stabilized solutions are available in concentrations from approximately 3.0% to 90.0% based on a weight/weight analysis. Concentrated hydrogen peroxide solutions ranging from about 30 to 50% by weight or greater are preferred for providing the bulk of the hydrogen peroxide source within the bleaching composition of the present invention. The higher the concentration of the initial hydrogen peroxide solution, the higher the final hydrogen peroxide concentration becomes within the final tooth whitening composition. Hydrogen peroxide solutions obtained from Solvay are the most preferred.

Due to the recent availability of linear and crosslinked Plasdone and Polyplasdone polymers complexed with hydrogen peroxide, also known as Polyvinylpyrrolidone (PVP)/hydrogen peroxide complexes or PEROXYDONE™ polymers manufactured by International Specialty Products, Inc. (ISP), aqueous peroxide solutions can be thickened while simultaneously increasing the available hydrogen peroxide concentration within the final composition. Higher levels of hydrogen peroxide translate into quicker bleaching times of vital teeth to obtain a desired tooth shade.

The stable, one-part, aqueous tooth whitening compositions of the present invention comprise hydrogen peroxide derived from multiple components within the composition. The compositions preferably comprise approximately 10% to 50% available hydrogen peroxide by weight of the total composition weight. In one form of the invention, an aqueous solution of 50% hydrogen peroxide is combined with a PVP/hydrogen peroxide complex to form an aqueous hydrogen peroxide gel or slurry. The 50% aqueous solution of hydrogen peroxide serves as the primary peroxide source for bleaching in the final composition, comprising about 75% to about 99% of the available hydrogen peroxide. A PVP/hydrogen peroxide complex preferably comprising from about 17% to 22% available hydrogen peroxide by weight of the complex serves as a secondary hydrogen peroxide source comprising about 1% to about 25% by weight of the available hydrogen peroxide in the final tooth whitening composition weight. This unique combination of hydrogen peroxide donor sources within the composition serves to contribute to the stability of the final tooth bleach composition. Omission of either hydrogen peroxide donor source from the bleach composition results in decomposition and ultimately failure of the composition at elevated temperature storage conditions. In addition, compositions that are generated omitting the polyplasdone/hydrogen peroxide complex result in failure of the bleach composition under room temperature storage conditions as well.

In the present invention, at least one thickening agent present may be provided to facilitate viscosity modification of the tooth bleaching compositions. In one preferred form of the invention, at least two thickening agents are present. The forming of a hydrogen peroxide gel serves as a two part function. First, a thickened composition prevents the peroxide from migrating from the surface of the tooth to the surrounding soft tissue which can lead to gingival sensitivity and burns. Second, it imparts an increase in retention time that the peroxide solution maintains its strength for release to the surface of the tooth.

In addition to a hydrogen peroxide source, the PVP/hydrogen peroxide complex also serves as a thickening agent for the composition. It is preferably present within the composition at about 1% to 25% by weight of the total composition weight. More preferably the thickening agent is present in the composition at about 5.0% to 20.0% by weight of the total composition. At this level, the PVP complex thickens the aqueous hydrogen peroxide to form a creamy paste or sticky gel of appropriate viscosity. The addition of a polyacrylic acid polymer as a secondary thickening agent allows the gel to be tailored to one of short rheological flow and increased bioadhesion to ensure that the final composition clings to the surface of the teeth. The addition of the polyacrylic acid polymer utilizes a crosslinked structure to prevent syneresis that may occur within the composition over an extended period of time, thus increasing overall gel stability.

In the present invention, the more preferred PVP/hydrogen peroxide complex is the crosslinked polyplasdone polymer. The crosslinked polyplasdone polymers exhibit insolubility in water, however, they swell rapidly in the presence of water to form a thickened matrix. As such, the hydrogen peroxide is easily dissociated from the polyplasdone polymer, thus releasing it to the surrounding aqueous media for bleaching availability. The preferred polyplasdone/hydrogen peroxide complex is marketed by International Specialty Products Corporation under the trade name PEROXYDONE XL-10 and maintains a particle size limit of approximately 60-100 microns.

It is known that polyacrylic acid polymers exhibit a high degree of incompatibility with certain ingredients such as PVP resins which are essential to the invention at hand. PVP polymers complex with un-neutralized polyacrylic acid polymers to prevent ionization of the polymer backbone. Without ionization of the polymer, uncoiling of the polyacrylic acid molecule cannot take place. This uncoiling is required for thickening of aqueous solutions. For this reason, the tooth whitening composition of the present invention is preferably generated in distinct phases, with the neutralization of the polyacrylic acid polymer preferably taking place in a phase prior to and separate from the combination with the PVP/hydrogen peroxide complex. By incorporating the polyacrylic acid polymer into the composition after the PVP/hydrogen peroxide complex has been combined with the aqueous hydrogen peroxide, the level of polyacrylic acid can be significantly reduced within the end use whitening composition. The preferred composition comprises a polyacrylic acid polymer from about 0.01% to 1.50% by weight of the final composition.

The preferred composition may also include a combination of a carrier and an hygroscopic agent that enable the composition to retain its aqueous properties and work synergistically with the thickening agents in order to remain rheologically active. Carriers generally form the base of the whitening composition, enabling all of the subsequent ingredients to be contained in a uniform and homogeneous mass. As the term implies, an aqueous whitening composition comprises a water-based carrier which would contain water or water in combination with other carrier ingredients. In addition to water, other carrier ingredients may include, but are not limited to, humectants or hygroscopic agents such as polyols, including glycerol, sorbitol, polyethylene glycols, propylene glycol, and the like. Preferably, the hygroscopic agent comprises from approximately 1.0% to 10.0% by weight of the total composition weight.

Additionally, surface active agents such as wetting agents and emulsifiers, including ionic or non-ionic surfactants, may be included within the carrier base. In the whitening composition of the present invention, the carrier group is selected from purified water with deionized ultra-filtrated water the most preferred and a polyhydric alcohol, glycerin. This combination has proven to be the best combination for extended, elevated temperature stability.

The present tooth whitening composition also preferably contains at least one bleaching agent stabilizer. And, the use of two specific stabilizers enables the gel formula to survive extended periods of time at elevated storage temperature conditions. It has been well documented that the use of bleaching agent stabilizers, which mainly comprise chelating agents, can increase the stability of tooth whitening compositions. Bleaching agent stabilizers function primarily by tying up errant metal ions that can catalyze the decomposition process of hydrogen peroxide. Preferably, the bleaching agent stabilizer(s) comprises approximately from 0.01% to 1.00% by weight of the total composition weight. In addition, in the preferred embodiment, the chelating agent(s) comprises approximately from 0.01% to 0.50% by weight of the total composition weight. Examples of suitable bleaching agent stabilizers are aminocarboxylic acids and their salts such as EDTA, EDTA disodium, EDTA, tetrasodium, calcium disodium EDTA and similar EDTA compounds, carboxylic acids and their salts such as citric acid, gluconic acid, sodium citrate, sodium gluconate and the like as well as tin compounds such as sodium stannate and potassium stannate.

The preferred composition may also include ethylenediaminetetraacetic acid, disodium salt, also known as edetate disodium or disodium EDTA, in combination with 1-hydroxyethane-1,1-diphosphonic acid, referred more commonly to as etidronic acid. It is the combination of these two ingredients in a precise ratio to the available hydrogen peroxide within the formula that enables the stability of the composition to be attained. It has been found that a combination of these two bleaching agent stabilizers in a ratio of about 30 parts available hydrogen peroxide to about 1 part combined stabilizers up to about 40 parts available hydrogen peroxide to about 1 part combined stabilizers will produce an elevated temperature stable whitening gel for an excess of 12 weeks at 40 degrees C. for a bleach composition of the present invention with an available hydrogen peroxide content of about 28 to 32% of the total bleach composition. The preferred ratio for the composition is about 35:1 to about 40:1 available hydrogen peroxide to combined stabilizers, with a ratio of about 38:1 the most preferred. However, it has been shown that the ratio of available hydrogen peroxide to bleaching agent stabilizers will function as a sliding scale with a greater ratio existing for bleach compositions exhibiting lower available hydrogen peroxide concentrations and a lower ratio for compositions containing higher levels of available hydrogen peroxide content. This window will exist for the present invention until ultimately compositions formulated outside the acceptable window will fail under elevated temperature stability testing. For example, it has been shown that a tooth bleach gel composition of the present invention containing about 15-20% available hydrogen peroxide will exhibit stability of an excess of 9 weeks at 47 degrees C. with a ratio of about 45.63:1 to about 56.43:1 available hydrogen peroxide to bleaching agent stabilizers. Conversely, a tooth bleach gel of the present invention containing about 32-35% available hydrogen peroxide will exhibit stability in excess of 7 weeks at 40 degrees C. with a ratio of about 26.71:1 to about 32.59:1 available hydrogen peroxide to bleaching agent stabilizers. Thus, it can be assumed that tooth bleaching compositions of the present invention with hydrogen peroxide contents from about 15% to about 35% can remain stable under elevated storage temperature conditions from 40 degrees C. to 47 degrees C. by maintaining a ratio of about 25:1 to 60:1 hydrogen peroxide to bleaching agent stabilizers within the formula.

Formulas that have been generated utilizing ratios beyond these preferred ranges have resulted in predictable failure of the whitening composition at elevated storage temperatures. Sample formulas were prepared on a weight/weight basis utilizing identical ingredients, varying only the percentages of the stabilizers contained within the preparation. Formulas were all buffered to a final pH of approximately 6.0 to 6.5. Only formulas that contained the two above mentioned stabilizing agents, present in the above mentioned ratios of hydrogen peroxide to combined stabilizers, survived long term stability under elevated storage conditions.

The composition of the present invention also contains a basic agent which adjusts the pH of the final whitening composition. Strong bases generally are used to buffer the acidic nature of hydrogen peroxide solutions. Additionally, when forming gels with polyacrylic acids, neutralization of the polymer chain must occur for thickening to take place. Preferably, the neutralizing agent comprises from 0.5% to 5.00% by weight of the total composition weight. Suitable basic agents for tooth whitening compositions are sodium hydroxide, ammonium hydroxide, triethanol amine, monoethanol amine, potassium hydroxide, sodium carbonate, trisodium phosphate and the like. The preferred basic agent for the whitening composition at hand is ammonium hydroxide solution.

EXAMPLES OF THE PREFERRED COMPOSITION

The compositions of stable tooth whitening gels capable of maintaining stability at elevated storage temperatures for an extended period of time are as follows:

The formulas below were all mixed utilizing non-metal components in order to minimize the chance of introducing errant metal ions into the composition. All mix vessels, spatulas and storage containers were constructed of either high density polyethylene or polypropylene. Care was taken to mix all formulas slowly and methodically in separate phases with pure ingredients, minimizing the possibility of entrained air and the contamination of macro-particles with large surface areas such as dust.

The following formulas were blended, titrated for available hydrogen peroxide and filled into 3 cc clear, HDPE Lauer-lock syringes affixed with a plunger. All plunger locations were marked on the syring body in order to determine any movement of the plunger due to the decomposition of hydrogen peroxide into oxygen gas. Syringes were placed into a stability oven set to 40° C. with 55% relative humidity and observer daily for plunger movement or viscosity breakdown. Samples syringes were pulled at 2 weeks, 4 weeks, 6 weeks, 10 weeks and 12 weeks and titrated for available hydrogen peroxide. Viscosity observations were determined by extruding the whitening composition onto a glass slide and placing the slide in a vertical position to determine if the gel remained in tact for a 5 minute time period without cascading down the glass slide.

EXAMPLE 1

| Phase 1: | |
| --- | --- |
| 6.17% | Glycerin |
| 1.29% | Carbopol 934P NF |
| 12.81% | Disodium EDTA Solution (3%) in DIUF water |
| 12.83% | Etidronic Acid Solution (3%) in DIUF water |
| 1.38% | Ammonium Hydroxide Solution (26 Baumé) |
| Phase 2: | |
| 55.03% | Hydrogen Peroxide Solution 50% |
| 10.19% | Peroxydone XL-10 (PVP/H2O2 Complex) |
| Phase 3: | |

Add Phase 1 into Phase 2 with slow agitation
Mix until homogeneous
| 0.30% | Buffer pH to 6.0 to 6.5 with Ammonium Hydroxide Solution (26 Baumé) |
| --- | --- |

The above formula titrated to 29.90% available hydrogen peroxide with an initial pH of approximately 6.5. It survived for an excess of 12 weeks at 40° C. with no appreciable loss of hydrogen peroxide content, viscosity or pH. This formula provides a ratio of available hydrogen peroxide to peroxide stabilizers of approximately 38.37:1.

EXAMPLE 2

| Phase 1: | |
| --- | --- |
| 5.44% | Glycerin |
| 1.47% | Carbopol 934P NF |
| 13.01% | Disodium EDTA Solution (3%) in DIUF water |
| 13.17% | Etidronic Acid Solution (3%) in DIUF water |
| 1.29% | Ammonium Hydroxide Solution (26 Baumé) |
| Phase 2: | |
| 54.90% | Hydrogen Peroxide Solution 50% |
| 10.20% | Peroxydone XL-10 (PVP/H2O2 Complex) |
| Phase 3: | |

Add Phase 1 into Phase 2 with slow agitation
Mix until homogeneous
| 0.52% | Buffer pH to 6.0 to 6.5 with Ammonium Hydroxide Solution (26 Baumé) |
| --- | --- |

The above formula titrated to 29.37% available hydrogen peroxide with an initial pH of approximately 6.4. It survived for an excess of 12 weeks at 40° C. with no appreciable loss of hydrogen peroxide content, viscosity or pH. This formula provides a ratio of available hydrogen peroxide to peroxide stabilizers of approximately 38.19:1.

EXAMPLE 3

| Phase 1: | |
| --- | --- |
| 5.35% | Glycerin |
| 1.28% | Carbopol 934P NF |

| | |
|---|---|
| 12.79% | Disodium EDTA Solution (3%) in DIUF water |
| 12.72% | Etidronic Acid Solution (3%) in DIUF water |
| 2.12% | Ammonium Hydroxide Solution (30%) |
| | Phase 2: |
| 53.65% | Hydrogen Peroxide Solution 50% |
| 10.00% | Peroxydone XL-10 (PVP/H2O2 Complex) |
| | Phase 3: |

Add Phase 1 into Phase 2 with slow agitation
Mix until homogeneous
| 2.09% | Buffer pH to 6.0 to 6.5 with Ammonium Hydroxide Solution (30%) |
|---|---|

The above formula titrated to 27.92% available hydrogen peroxide with an initial pH of approximately 6.5. It survived for an excess of 12 weeks at 40° C. with no appreciable loss of hydrogen peroxide content, viscosity or pH. This formula provides a ratio of available hydrogen peroxide to peroxide stabilizers of approximately 37.35:1.

EXAMPLE 4

| | Phase 1: |
|---|---|
| 5.11% | Glycerin |
| 1.25% | Carbopol 934P NF |
| 12.49% | Disodium EDTA Solution (1%) in DIUF water |
| 12.53% | Etidronic Acid Solution (1%) in DIUF water |
| 2.07% | Ammonium Hydroxide Solution (30%) |
| | Phase 2: |
| 53.18% | Hydrogen Peroxide Solution 50% |
| 10.01% | Peroxydone XL-10 (PVP/H2O2 Complex) |
| | Phase 3: |

Add Phase 1 into Phase 2 with slow agitation
Mix until homogeneous
| 3.36% | Buffer pH to 6.0 to 6.5 with Ammonium Hydroxide Solution (30%) |
|---|---|

The above formula titrated to 28.23% available hydrogen peroxide with an initial pH of approximately 6.5. It survived for 9 days at 40° C. The plungers all were displaced from the syringe body with gel expelling from the syringe. The pH of the gel had dropped to approximately 5.0. This formula provides a ratio of available hydrogen peroxide to peroxide stabilizers of approximately 112.98:1.

EXAMPLE 5

| | Phase 1: |
|---|---|
| 5.44% | Glycerin |
| 1.28% | Carbopol 934P NF |
| 13.28% | Disodium EDTA Solution (5%) in DIUF water |
| 13.18% | Etidronic Acid Solution (5%) in DIUF water |
| 1.19% | Ammonium Hydroxide Solution (26 Baumé) |
| | Phase 2: |
| 53.59% | Hydrogen Peroxide Solution 50% |
| 10.21% | Peroxydone XL-10 (PVP/H2O2 Complex) |

| | Phase 3: |
|---|---|

Add Phase 1 into Phase 2 with slow agitation
Mix until homogeneous
| 1.83% | Buffer pH to 6.0 to 6.5 with Ammonium Hydroxide Solution (26 Baumé) |
|---|---|

The above formula titrated to 28.43% available hydrogen peroxide with an initial pH of approximately 6.4. It survived for 6 weeks 4 days at 40° C. The plungers all were displaced from the syringe body with gel expelling from the syringe. The pH of the gel had dropped to approximately 5.2. This formula provides a ratio of available hydrogen peroxide to peroxide stabilizers of approximately 21.68:1.

EXAMPLE 6

| | Phase 1: |
|---|---|
| 7.08% | Glycerin |
| 1.37% | Carbopol 934P NF |
| 17.12% | Disodium EDTA Solution (1%) in DIUF water |
| 17.15% | Etidronic Acid Solution (1%) in DIUF water |
| 0.93% | Ammonium Hydroxide Solution (26 Baumé) |
| | Phase 2: |
| 44.57% | Hydrogen Peroxide Solution 35% |
| 7.27% | Peroxydone XL-10 (PVP/H2O2 Complex) |
| | Phase 3: |

Add Phase 1 into Phase 2 with slow agitation
Mix until homogeneous
| 4.51% | Buffer pH to 6.0 to 6.5 with Ammonium Hydroxide Solution (26 Baumé) |
|---|---|

The above formula titrated to 17.142% available hydrogen peroxide with an initial pH of approximately 6.4. It survived for an excess of 9 weeks at 47° C. with no appreciable loss of hydrogen peroxide content, viscosity or pH. This formula provides a ratio of available hydrogen peroxide to peroxide stabilizers of approximately 49.63:1.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed:

1. A one-part, aqueous tooth bleaching composition for contacting a tooth surface comprising:
   hydrogen peroxide solution;
   a crosslinked polyvinylpyrrolidone/hydrogen peroxide complex;
   a bleaching agent stabilizer; and
   at least 50% by weight of water;
   wherein the composition maintains greater than 95% available hydrogen peroxide content after 12 weeks storage at 40 degrees C. with no loss of gel viscosity.

2. The tooth bleaching composition according to claim 1, wherein the bleaching agent stabilizer comprises a 1:1 ratio by weight of ethylenediaminetetraacetic acid disodium salt and etidronic acid.

3. The tooth bleaching composition according to claim 2, wherein the ratio by weight of hydrogen peroxide to bleaching agent stabilizer is about 25:1 to about 60:1.

4. The tooth bleaching composition according to claim 1, wherein the ratio of hydrogen peroxide by weight to bleaching agent stabilizer is about 25:1 to about 60:1.

5. The tooth bleaching composition according to claim 1, wherein the polyvinylpyrrolidone/hydrogen peroxide complex comprises at least 10.0% by weight of the total composition weight.

6. The tooth bleaching composition according to claim 1, wherein the bleaching agent stabilizer is selected from a group consisting of ethylenediamineteraacetic acid, disodium salt; ethylenediamineteraacetic acid, tetrasodium salt; ethylenediaminetetraacetic acid, calcium disodium salt; etidronic acid; citric acid; gluconic acid; sodium citrate; sodium gluconate; sodium phosphate; disodium phosphate; trisodium phosphate; tetrapotassium pyrophosphate; sodium tripolyphosphate and potassium stannate.

7. The tooth bleaching composition according to claim 1, further comprising at least one chelating agent selected from the group consisting of ethylenediamineteraacetic acid, disodium salt; ethylenediamineteraacetic acid, tetrasodium salt; ethylenediaminetetraacetic acid, calcium disodium salt; citric acid; gluconic acid; sodium citrate; sodium gluconate; sodium phosphate; disodium phosphate; trisodium phosphate; tetrapotassium pyrophosphate; and sodium tripolyphosphate.

8. The tooth bleaching composition according to claim 7, wherein the at least one chelating agent comprises from about 0.01% to about 0.50% by weight of the total composition weight.

9. The tooth bleaching composition according to claim 1, further comprising at least one chelating agent, the chelating agent being disodium EDTA.

10. The tooth bleaching composition according to claim 1, further comprising at least one hygroscopic agent selected from the polyol group consisting of glycerin, polyethylene glycol, propylene glycol and sorbitol.

11. The tooth bleaching composition according to claim 10, wherein the at least one hydroscopic agent comprises from about 1.0% to about 10.0% by weight of the total composition weight.

12. The tooth bleaching composition according to claim 11, wherein the at least one hygroscopic agent is glycerin.

13. The tooth bleaching composition according to claim 1, further comprising at least one neutralizing agent selected from a group consisting of triethanolamine, tromethamine, sodium hydroxide, potassium hydroxide, and ammonium hydroxide.

14. The tooth bleaching composition according to claim 13, wherein the at least one neutralizing agent adjusts the pH of the final tooth whitening composition between about 6.0 to about 7.0.

15. The tooth bleaching composition according to claim 13, wherein the at least one neutralizing agent comprises from about 0.50% to about 5.00% by weight of the total composition weight.

16. The tooth bleaching composition according to claim 13, wherein the at least one neutralizing agent is ammonium hydroxide.

17. The tooth bleaching composition according to claim 1, further comprising at least one chelating agent, the chelating agent being etidronic acid.

* * * * *